(12) United States Patent
Germain et al.

(10) Patent No.: US 10,349,815 B2
(45) Date of Patent: *Jul. 16, 2019

(54) FLUID MANAGEMENT SYSTEMS AND METHODS

(71) Applicant: BOSTON SCIENTIFIC SCIMED, INC., Maple Grove, MN (US)

(72) Inventors: Aaron Germain, Campbell, CA (US); Michael D. Walker, San Francisco, CA (US); Jacob Roland, San Jose, CA (US); Jan Echeverry, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,031

(22) Filed: Dec. 19, 2018

(65) Prior Publication Data

US 2019/0117043 A1    Apr. 25, 2019

Related U.S. Application Data

(63) Continuation of application No. 15/245,940, filed on Aug. 24, 2016, now Pat. No. 10,178,942.

(Continued)

(51) Int. Cl.
*A61M 3/02* (2006.01)
*A61B 1/00* (2006.01)
(Continued)

(52) U.S. Cl.
CPC ...... *A61B 1/00055* (2013.01); *A61B 1/00057* (2013.01); *A61B 1/015* (2013.01); *A61B 1/303* (2013.01); *A61B 18/149* (2013.01); *A61B 18/1492* (2013.01); *A61M 5/16827* (2013.01); *A61M 5/16845* (2013.01);
(Continued)

(58) Field of Classification Search
None
See application file for complete search history.

(56) References Cited

U.S. PATENT DOCUMENTS

| | | |
|---|---|---|
| 3,939,360 A | 2/1976 | Jackson |
| 4,116,198 A | 9/1978 | Roos |

(Continued)

FOREIGN PATENT DOCUMENTS

| | | |
|---|---|---|
| WO | 2009009398 A1 | 1/2009 |
| WO | 2012031630 A1 | 3/2012 |

*Primary Examiner* — Brent Swarthout
(74) *Attorney, Agent, or Firm* — Seager, Tufte & Wickhem, LLP

(57) ABSTRACT

Systems, devices, and methods for fluid management in an endoscopic procedure are disclosed. In one embodiment, a fluid management device may comprise a pair of electrodes and a controller connected to the pair of electrodes. In at least some embodiments, the controller may be configured to receive signals from the pair of electrodes and determine whether a fluid in a fluid reservoir is an ionic fluid or a non-ionic fluid based on signals received from the pair of electrodes. In at least some additional embodiments, the controller may be further configured to automatically set a fluid deficit alarm threshold based on the determination of whether the fluid in the fluid reservoir is an ionic fluid or a non-ionic fluid.

20 Claims, 12 Drawing Sheets

Related U.S. Application Data

(60) Provisional application No. 62/210,836, filed on Aug. 27, 2015.

(51) Int. Cl.
*A61B 1/303* (2006.01)
*A61B 18/14* (2006.01)
*A61M 5/168* (2006.01)
*A61M 5/172* (2006.01)
*A61B 1/015* (2006.01)
*A61B 18/00* (2006.01)
*A61B 90/00* (2016.01)

(52) U.S. Cl.
CPC ... *A61M 5/172* (2013.01); *A61B 2018/00029* (2013.01); *A61B 2018/00601* (2013.01); *A61B 2018/00607* (2013.01); *A61B 2018/00648* (2013.01); *A61B 2018/00666* (2013.01); *A61B 2018/00744* (2013.01); *A61B 2018/00875* (2013.01); *A61B 2018/00892* (2013.01); *A61B 2018/00898* (2013.01); *A61B 2090/0807* (2016.02); *A61M 2205/18* (2013.01); *A61M 2205/60* (2013.01)

(56) References Cited

U.S. PATENT DOCUMENTS

| | | | |
|---|---|---|---|
| 4,449,538 A | 5/1984 | Corbitt et al. | |
| 4,628,302 A * | 12/1986 | Barr | G01F 23/241 324/678 |
| 4,706,656 A | 11/1987 | Kuboto | |
| 4,994,026 A | 2/1991 | Fecondini | |
| 4,998,527 A | 3/1991 | Meyer | |
| 5,152,746 A | 10/1992 | Atkinson et al. | |
| 5,176,629 A | 1/1993 | Kullas et al. | |
| 5,312,399 A | 5/1994 | Hakky et al. | |
| 5,382,229 A | 1/1995 | Grabenkort et al. | |
| 5,392,765 A | 2/1995 | Muller | |
| 5,437,629 A | 8/1995 | Goldrath | |
| 5,445,610 A | 8/1995 | Evert | |
| 5,456,689 A | 10/1995 | Kresch et al. | |
| 5,492,537 A | 2/1996 | Vancaillie | |
| 5,503,626 A | 4/1996 | Goldrath | |
| 5,522,805 A | 6/1996 | Vancaillie et al. | |
| 5,556,378 A | 9/1996 | Storz et al. | |
| 5,586,973 A | 12/1996 | Lemaire et al. | |
| 5,709,670 A | 1/1998 | Vancaillie et al. | |
| 5,807,240 A | 9/1998 | Muller et al. | |
| 5,814,009 A | 9/1998 | Wheatman | |
| 5,836,909 A | 11/1998 | Cosmescu | |
| 5,885,277 A | 3/1999 | Korth | |
| 5,921,953 A | 7/1999 | Novak et al. | |
| 5,944,668 A | 8/1999 | Vancaillie et al. | |
| 5,947,990 A | 9/1999 | Smith | |
| 6,032,673 A | 3/2000 | Savage et al. | |
| 6,039,748 A | 3/2000 | Savage et al. | |
| 6,113,594 A | 9/2000 | Savage | |
| 6,113,597 A | 9/2000 | Eggers et al. | |
| 6,159,160 A | 12/2000 | Hsei et al. | |
| 6,238,366 B1 | 5/2001 | Savage et al. | |
| 6,319,221 B1 | 5/2001 | Lee | |
| 6,979,332 B2 | 12/2005 | Adams | |
| 7,207,966 B2 | 4/2007 | Savare et al. | |
| 7,429,262 B2 | 9/2008 | Woloszko et al. | |
| 7,678,070 B2 | 3/2010 | Kumar et al. | |
| 7,918,822 B2 | 4/2011 | Kumar et al. | |
| 8,061,359 B2 | 11/2011 | Emanuel | |
| 8,062,214 B2 | 11/2011 | Shener et al. | |
| 8,226,549 B2 | 7/2012 | Kumar et al. | |
| 8,308,726 B2 | 11/2012 | Kumar et al. | |
| 8,388,570 B2 | 3/2013 | Kumar et al. | |
| 8,419,626 B2 | 4/2013 | Shener-Irmakoglu et al. | |
| 8,444,592 B2 | 5/2013 | Williams et al. | |
| 8,460,178 B2 | 6/2013 | Kumar et al. | |
| 8,512,283 B2 | 8/2013 | Kumar et al. | |
| 8,512,326 B2 | 8/2013 | Shadduck et al. | |
| 8,568,424 B2 | 10/2013 | Shugrue et al. | |
| 8,591,464 B2 | 11/2013 | Kumar et al. | |
| 8,597,228 B2 | 12/2013 | Pyles et al. | |
| 8,652,089 B2 | 2/2014 | Kumar et al. | |
| 8,728,066 B2 | 5/2014 | Shadduck et al. | |
| 8,790,303 B2 | 7/2014 | Williams et al. | |
| 8,840,625 B2 | 9/2014 | Adams et al. | |
| 8,840,626 B2 | 9/2014 | Adams et al. | |
| 8,852,085 B2 | 10/2014 | Shener-Irmakoglu et al. | |
| 8,911,363 B2 | 12/2014 | Kumar et al. | |
| 8,951,274 B2 | 2/2015 | Adams et al. | |
| 8,974,448 B2 | 3/2015 | Germain et al. | |
| 9,028,398 B2 | 5/2015 | Kumar et al. | |
| 9,060,760 B2 | 6/2015 | Sullivan et al. | |
| 9,072,431 B2 | 7/2015 | Adams et al. | |
| 9,084,847 B2 | 7/2015 | Klein et al. | |
| 9,095,366 B2 | 8/2015 | Sullivan et al. | |
| 9,155,453 B2 | 10/2015 | Kumar et al. | |
| 9,233,193 B2 | 1/2016 | Truckai et al. | |
| 9,254,142 B2 | 2/2016 | Germain et al. | |
| 9,272,086 B2 | 3/2016 | Williams et al. | |
| 9,439,677 B2 | 9/2016 | Germain et al. | |
| 9,439,720 B2 | 9/2016 | Germain et al. | |
| 9,474,848 B2 | 10/2016 | Williams et al. | |
| 9,486,233 B2 | 11/2016 | Bek et al. | |
| 9,498,244 B2 | 11/2016 | Orczy-Timko et al. | |
| 9,549,754 B2 | 1/2017 | Shadduck et al. | |
| 10,178,942 B2 * | 1/2019 | Germain | A61B 1/00055 |
| 2002/0032403 A1 | 3/2002 | Savagle et al. | |
| 2002/0038122 A1 | 3/2002 | Peters | |
| 2007/0038112 A1 | 10/2007 | Sohn et al. | |
| 2008/0249366 A1 | 10/2008 | Gruber et al. | |
| 2009/0270895 A1 | 10/2009 | Churchill et al. | |
| 2009/0270896 A1 | 10/2009 | Sullivan et al. | |
| 2011/0166510 A1 | 7/2011 | Feng et al. | |
| 2012/0078038 A1 | 3/2012 | Sahney et al. | |
| 2013/0046304 A1 | 2/2013 | Germain et al. | |
| 2013/0079702 A1 | 3/2013 | Klein et al. | |
| 2013/0103021 A1 | 4/2013 | Germain et al. | |
| 2013/0172805 A1 | 4/2013 | Germain et al. | |
| 2013/0172870 A1 | 7/2013 | Germain et al. | |
| 2013/0197471 A1 | 8/2013 | Williams et al. | |
| 2013/0231652 A1 | 9/2013 | Germain et al. | |
| 2013/0296847 A1 | 11/2013 | Germain et al. | |
| 2014/0031834 A1 | 1/2014 | Germain et al. | |
| 2014/0114300 A1 | 4/2014 | Orczy-Timko et al. | |
| 2014/0221997 A1 | 8/2014 | Shadduck et al. | |
| 2014/0303551 A1 | 10/2014 | Germain et al. | |
| 2014/0324065 A1 | 10/2014 | Bek et al. | |
| 2015/0119795 A1 | 4/2015 | Germain et al. | |
| 2015/0157396 A1 | 6/2015 | Germain et al. | |
| 2015/0314048 A1 | 11/2015 | Klein et al. | |
| 2015/0328379 A1 | 11/2015 | Carr et al. | |
| 2016/0089184 A1 | 3/2016 | Truckai et al. | |
| 2016/0106497 A1 | 4/2016 | Germain et al. | |
| 2016/0317219 A1 | 11/2016 | Germain et al. | |
| 2017/0000957 A1 | 1/2017 | Carr et al. | |
| 2017/0014180 A1 | 1/2017 | Germain et al. | |
| 2017/0203028 A1 | 7/2017 | Carr et al. | |

\* cited by examiner

FLUID MANAGEMENT SYSTEMS AND METHODS

CROSS-REFERENCE TO RELATED APPLICATIONS

This application is a continuation of U.S. patent application Ser. No. 15/245,940, filed Aug. 24, 2016, now U.S. Pat. No. 10,178,942, which claims priority under 35 U.S.C. § 119 to U.S. Provisional Application Ser. No. 62/210,836, filed Aug. 27, 2015, the entirety of which is incorporated herein by reference.

TECHNICAL FIELD

The present invention relates to surgical fluid management systems and methods, for example for use in distending the uterine cavity to allow resection and extraction of abnormal uterine tissue such as fibroids and polyps.

BACKGROUND

Fibroids are non-cancerous tumors that develop in the wall of uterus. Uterine fibroids in particular occur in a large percentage of the female population, with some studies indicating up to 40 percent of all women have fibroids. Such fibroids can grow over time to be several centimeters in diameter and symptoms can include menorrhagia, reproductive dysfunction, pelvic pressure and pain.

One current treatment of fibroids is endoscopic or hysteroscopic resection or myomectomy. In relation to uterine fibroids, this involves transcervical access to the uterus with a hysteroscope together with insertion of a resecting instrument through a working channel in the hysteroscope. The resecting instrument may be an electrosurgical resection device such as an RF cutting loop. An electrosurgical resecting device is disclosed in U.S. Pat. No. 5,906,615. In other instances, a mechanical cutter may be used to mechanically cut tissue. Mechanical cutting devices are disclosed in U.S. Pat. Nos. 7,226,459; 6,032,673 and 5,730,752 and U.S. Published Patent Appl. 2009/0270898.

In a resection procedure, one step of the procedure includes distention of the operating cavity to create a working space for the procedure. In a relaxed state, body cavities tend to collapse with opposing walls in contact with one another. A fluid management system is used to distend the operating cavity to provide a working space. Fluid is administered through a passageway in the endoscope or hysteroscope or another device under sufficient pressure to expand or distend the body cavity. In some instances, the administered fluid may be taken up by the body, such as through an exposed blood vessel, which may be termed intravasation. In general, this fluid uptake is undesirable and can even cause serious complications or even death.

SUMMARY

The present disclosure is generally directed toward devices and methods for managing fluid used to inflate a body cavity of a patient during an endoscopic procedure. In one embodiment, a fluid management device may comprise a pair of electrodes and a controller connected to the pair of electrodes. The controller may be configured to receive signals from the pair of electrodes and determine whether a fluid in a fluid reservoir is an ionic fluid or a non-ionic fluid based on signals received from the pair of electrodes. In at least some additional embodiments, the controller may further be configured to automatically set a fluid deficit alarm threshold based on the determination of whether the fluid in the fluid reservoir is an ionic fluid or a non-ionic fluid.

Alternatively, or additionally, in any of the above previous embodiments, the controller may further determine that the fluid in the fluid reservoir is an ionic fluid if the capacitance is lower than a threshold and determine that the fluid in the fluid reservoir is a non-ionic fluid if the capacitance is greater than or equal to the threshold.

Alternatively, or additionally, in any of the above previous embodiments, the fluid deficit alarm threshold may have a first value if the controller determined the that the fluid in the fluid reservoir is an ionic fluid and the fluid deficit alarm threshold may have a second value if the controller determined that the fluid in the fluid reservoir is a non-ionic fluid, wherein the first value and the second value are different.

Alternatively, or additionally, in any of the above previous embodiments, the first value may be between about 2 liters and about 3 liters, and wherein the second value may be between about 0.5 liters and 1.5 liters.

Alternatively, or additionally, in any of the above previous embodiments, the device may further comprise a capacitance-measuring module connected between the two electrodes and the controller.

Alternatively, or additionally, in any of the above previous embodiments, the device may further comprise a patch, wherein the patch contains the two electrodes separated by a distance.

Alternatively, or additionally, in any of the above previous embodiments, a surface of the patch may comprise a biohazard symbol.

Alternatively, or additionally, in any of the above previous embodiments, the patch may be an adhesive patch.

Alternatively, or additionally, in any of the above previous embodiments, the controller may be further configured to compare a fluid deficit value to the fluid deficit alarm threshold, and output an alarm signal after determining that the fluid deficit value is greater than the fluid deficit alarm threshold.

Alternatively, or additionally, in any of the above previous embodiments, the alarm signal may be configured to one or more of: cause a user interface device to display an indication the fluid deficit value has reached or exceeded the fluid deficit alarm threshold, cause a user interface device to generate an audible alarm, and prevent fluid from being pumped out of the reservoir.

Alternatively, or additionally, in any of the above previous embodiments, the device may further comprise a weight-measuring device connected to the controller, wherein the controller is further configured to determine the fluid deficit value based on signals received from the weight-measurement device.

Alternatively, or additionally, in any of the above previous embodiments, the device may further comprise a user interface device, wherein the controller is configured to output for display at the user interface device, the fluid deficit value.

In another embodiment, a fluid management method may comprise receiving electrical signals via two electrodes, determining a capacitance based on the received electrical signals, and determining, based on the determined capacitance, whether a fluid in a fluid reservoir is an ionic fluid or a non-ionic fluid. In at least some additional embodiments, the method may further comprise outputting a signal indicating that the fluid is either ionic or non-ionic.

Alternatively, or additionally, in any of the above previous embodiments, the method may further comprise setting a maximum fluid deficit threshold at a first value based on a determination that the fluid in the fluid reservoir is an ionic fluid and setting the maximum fluid deficit threshold at a second value based on a determination that the fluid in the fluid reservoir is a non-ionic fluid. In at least some embodiments, the first value and the second value are different.

Alternatively, or additionally, in any of the above previous embodiments, the method may further comprise receiving a weight signal from a weight-measuring device, determining a fluid deficit parameter based on the weight signal, and comparing the fluid deficit parameter to a maximum fluid deficit threshold. In at least some embodiments, the method may additionally comprise outputting an alert signal after determining the fluid deficit parameter is above the maximum fluid deficit threshold.

In still another embodiments, a fluid management system may comprise a weight-measuring device, two electrodes, and a controller connected to the electrodes and to the weight-measuring device. In at least some embodiments, the controller may be configured to receive signals via the electrodes and from the weight-measuring device and determine whether a fluid in a fluid reservoir is an ionic fluid or a non-ionic fluid based on signals received from the electrodes. In still additional embodiments, the controller may be further configured to automatically set a fluid loss alarm threshold based on the determination of whether the fluid in the fluid reservoir is an ionic fluid or a non-ionic fluid, determine a fluid loss parameter based on signals received from the weight-measuring device, and compare the fluid loss parameter to the fluid loss alarm threshold. Some embodiments may have the method further generating an indication the fluid loss parameter has exceeded the fluid loss alarm threshold after determining the fluid loss parameter is greater than the fluid loss alarm threshold.

Alternatively, or additionally, in any of the above previous embodiments, the fluid loss alarm threshold may have a first value if the controller determined the that the fluid in the fluid reservoir is an ionic fluid and the fluid loss alarm threshold may have a second value if the controller determined that the fluid in the fluid reservoir is a non-ionic fluid, wherein the first value and the second value are different.

Alternatively, or additionally, in any of the above previous embodiments, the fluid loss parameter may be based on a difference in a previous weight signal received from the weight-measuring device and a current weight signal received from the weight-measuring device.

Alternatively, or additionally, in any of the above previous embodiments, the system may further comprise a pump connected to the controller, and the indication may comprise the controller preventing the pump from pumping.

Alternatively, or additionally, in any of the above previous embodiments, the system may further comprise a user interface device connected to the controller, and the indication may comprise displaying, at the user interface device, an indication that the fluid loss parameter has exceeded the fluid loss alarm threshold.

Alternatively, or additionally, in any of the above previous embodiments, the system may further comprise a patch, the patch containing the two electrodes separated by a distance.

The above summary of some embodiments is not intended to describe each disclosed embodiment or every implementation of the present invention. The Figures, and Detailed Description, which follow, more particularly exemplify these embodiments.

BRIEF DESCRIPTION OF DRAWINGS

The invention may be more completely understood in consideration of the following detailed description of various embodiments of the invention in connection with the accompanying drawings, in which.

Figure 1:
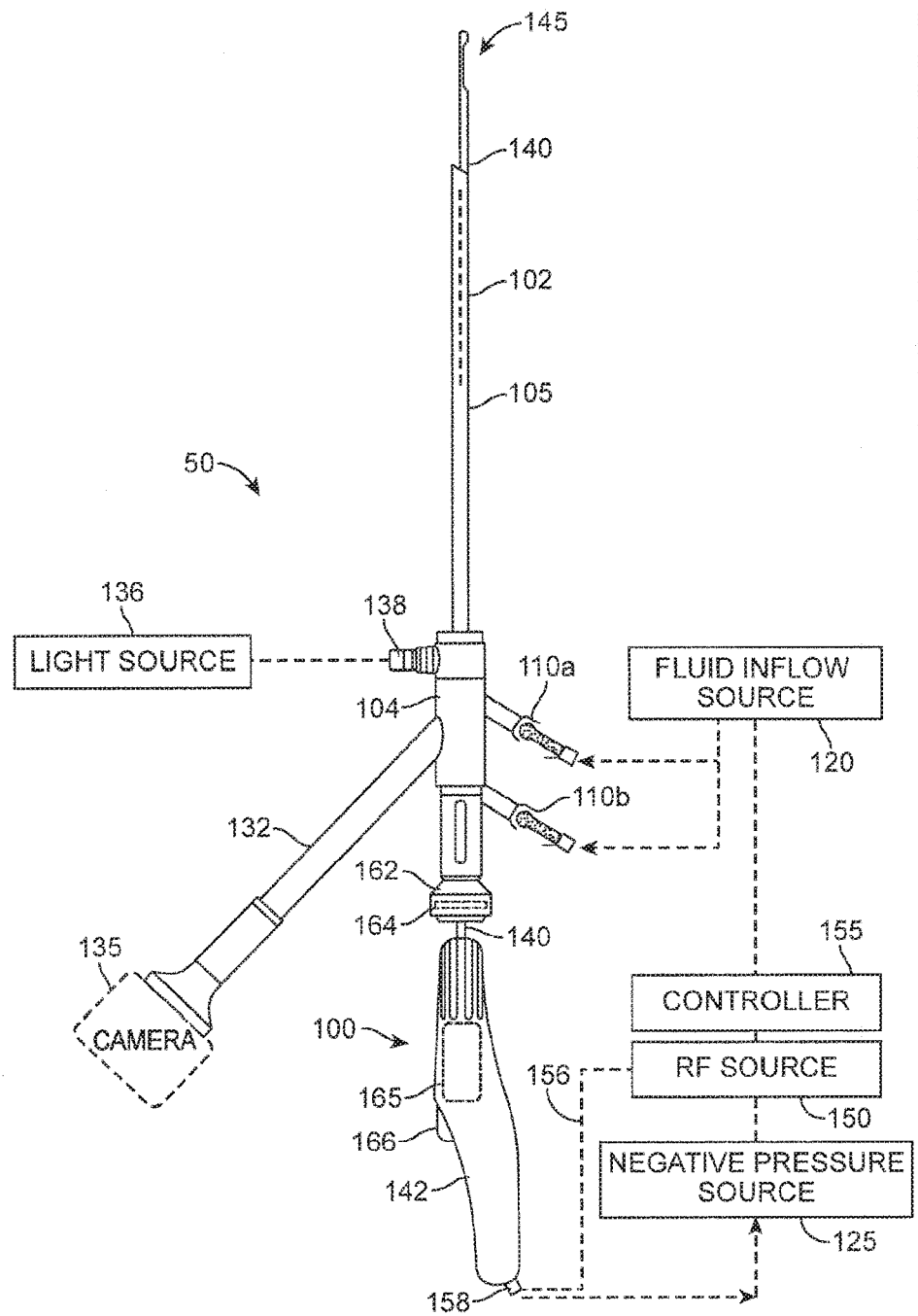
FIG. 1 is a plan view of an assembly including a hysteroscope and a tissue-resecting device inserted through the working channel of the hysteroscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Figure 2:
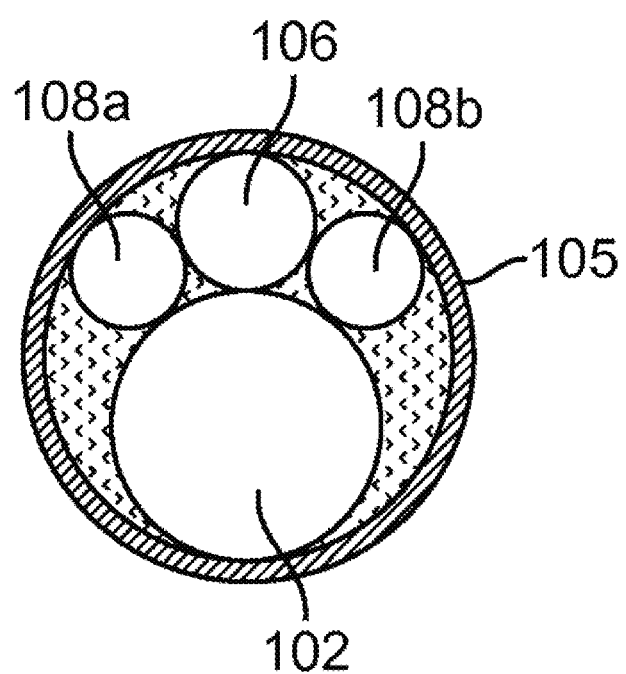
FIG. 2 is a cross-sectional view of the shaft of the hysteroscope of FIG. 1 showing various channels extending through at least a portion of the hysteroscope.

FIG. 1 illustrates an assembly that comprises an endoscope or hysteroscope 50 that may be used for hysteroscopy together with a tissue resecting device 100 extending through a working channel 102 of the hysteroscope. The hysteroscope 50 has a handle 104 coupled to an elongated shaft 105 and may have a diameter of 5 mm to 7 mm. The working channel 102 therein may be round, D-shaped or any other suitable shape. The elongated shaft 105 is further configured with a channel 106, which may used as an optics channel or a static pressure channel, as described in more detail below, and one or more fluid inflow/outflow channels 108a, 108b (FIG. 2). The one or more fluid inflow/outflow channels 108a, 108b may communicate with valve-connectors 110a, 110b configured for coupling to a fluid inflow source 120, or optionally a negative pressure source 125.

The fluid inflow source 120 may comprise a fluid container or reservoir 128 and fluid 129 contained within the fluid reservoir 128. The fluid source 120 may be connected to a fluid management system 126 (FIG. 3) which comprises pump mechanisms 130a and 130b to pump the fluid through the hysteroscope 50 into the uterine cavity and/or out of the uterine cavity. Exemplary closed system fluid management systems are described in US 2013/0172805, US 2013/0079702, US 2014/0303551 and US 2015/0119795, each of which is herein incorporated by reference in its entirety.

The handle 104 of the hysteroscope 50 can include angled extension portion 132 with optics to which a videoscopic camera 135 can be operatively coupled. A light source 136 may further be coupled to light coupling 138 on the handle of the hysteroscope 50. The working channel 102 of the hysteroscope is generally configured for insertion and manipulation of the tissue-resecting device 100, for example to treat and remove fibroid tissue. In one embodiment, the elongated shaft 105 has an axial length of 21 cm, and can comprise a 0° scope, or 15° to 30° scope. However, in other embodiments, the dimensions of elongated shaft 105 may differ.

Still referring to FIG. 1, the tissue-resecting device 100 may have a highly elongated shaft assembly 140 configured to extend through the working channel 102 in the hysteroscope 50. A handle 142 of the tissue-resecting device 100 may be adapted for manipulating the electrosurgical working end 145 of the device. In use, the handle 142 can be manipulated both rotationally and axially, for example, to orient the working end 145 to resect targeted fibroid tissue. Where tissue-resecting device 100 is an electrosurgical device, tissue-resecting device 100 may have subsystems coupled to its handle 142 to enable electrosurgical resecting of targeted tissue. In these embodiments, a radiofrequency generator or RF source 150 and controller 155 may be coupled to at least one RF electrode carried by the working end. In one embodiment shown in FIG. 1, an electrical cable 156 and negative pressure source 125 are operatively coupled to a connector 158 in handle 142. The electrical cable 156 couples the RF source 150 to the electrosurgical working end 145. The negative pressure source 125 communicates with a tissue extraction channel in the shaft assembly 140 of the tissue extraction device 100. Exemplary tissue resection devices are described in U.S. Pat. No. 8,512,326, US 2014/0221997, US 2013/0046304, and US 2014/0114300, each of which is herein incorporated by reference in its entirety.

FIG. 1 further illustrates a seal housing 162 that hysteroscope 50 may include which carries a flexible seal 164 carried by the hysteroscope handle 104 for sealing the shaft 140 of the tissue-resecting device 100 in the working channel 102 to prevent distending fluid from escaping from a uterine cavity.

In at least one embodiment as shown in FIG. 1, the handle 142 of tissue-resecting device 100 may include a motor drive 165 for reciprocating or otherwise moving a resecting component of the electrosurgical working end 145. The handle 142 may optionally include one or more actuator buttons 166 for actuating the device. In another embodiment, a footswitch can be used to operate the device. In various embodiments, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating resecting sleeve in a non-extended position and in an extended position. Additionally, or alternatively, the system can include a mechanism for actuating a single reciprocating stroke.

Figure 3:
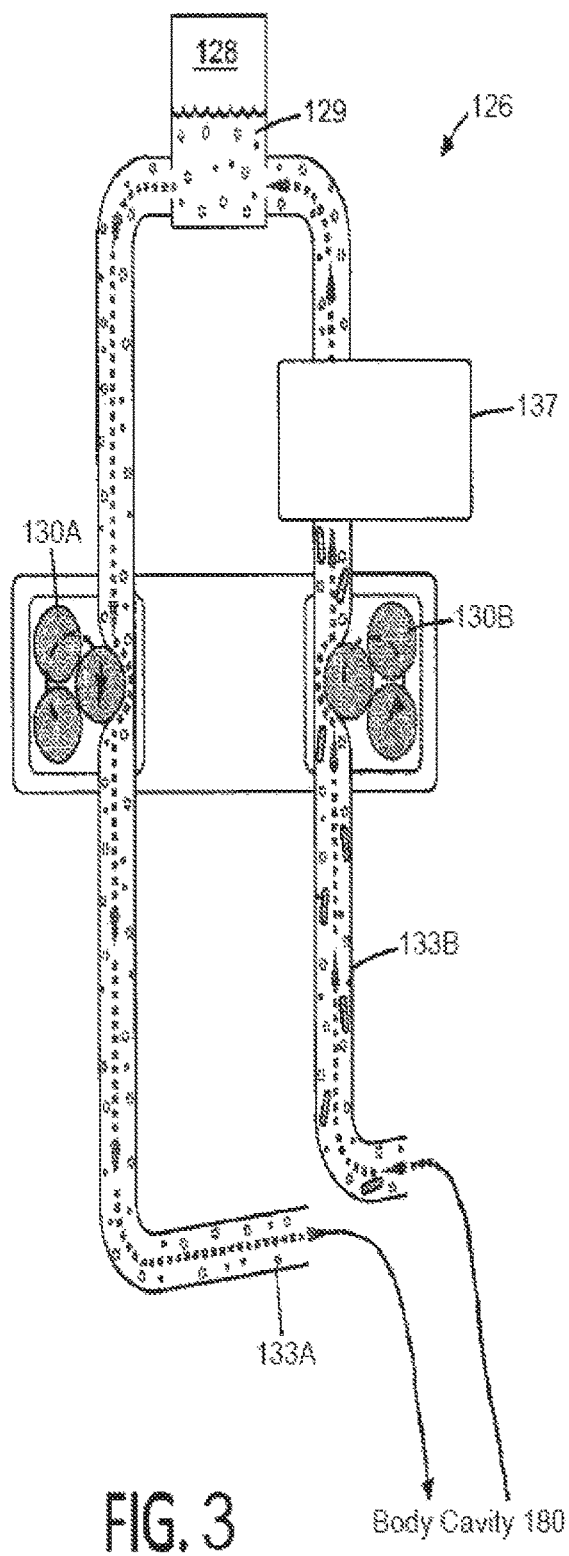
FIG. 3 is a schematic view of a fluid management system used for distending the uterus and for assisting in tissue resection and extraction.

As discussed, a fluid management system, such as fluid management system 126 shown in FIG. 3 may be used with the hysteroscope 50 and/or the tissue-resecting device 100. FIG. 3 depicts a closed fluid management system where the distension fluid 129 is recirculated for use during a procedure. For example, a pump 130A may be a peristaltic pump, or any other suitable pump mechanism, and may be connected to the fluid flow line 133A so as to pump fluid from fluid the reservoir 128 through the fluid flow line 133A to the body cavity 180. Conversely, a pump 130b may be a peristaltic pump, or any other suitable pump mechanism, and may be connected to the fluid flow line 133B so as to pump fluid out of the body cavity 180 through the fluid flow line 133B to the fluid reservoir 128. In some embodiments, the fluid flow system 126 may have a filter 137 to filter out tissue and other particles that may be present in the return fluid 129 before returning the fluid 129 to the fluid reservoir 128.

In different procedures, different distending fluids having different properties may be used in the fluid management system 126 based on the desired function of the distending fluid, the type of resection device, or other factors. In some instances, the distending fluid may be an ionic fluid, while in other instances the distending fluid may be a non-ionic fluid. Allowable limits of intravasation of the distending fluid may be different depending on whether the fluid is an ionic fluid or a non-ionic fluid. For instance, uptake of no more than 2.5 L of an ionic fluid may be considered safe while uptake of no more than only 1.0 L of a non-ionic fluid may be considered safe. Accordingly, in some embodiments, a control device, such as a control device 200 as shown in FIG. 4, may be used with a fluid management system, such as fluid management system 126 in order to monitor fluid intravasation or uptake.

Figure 4:
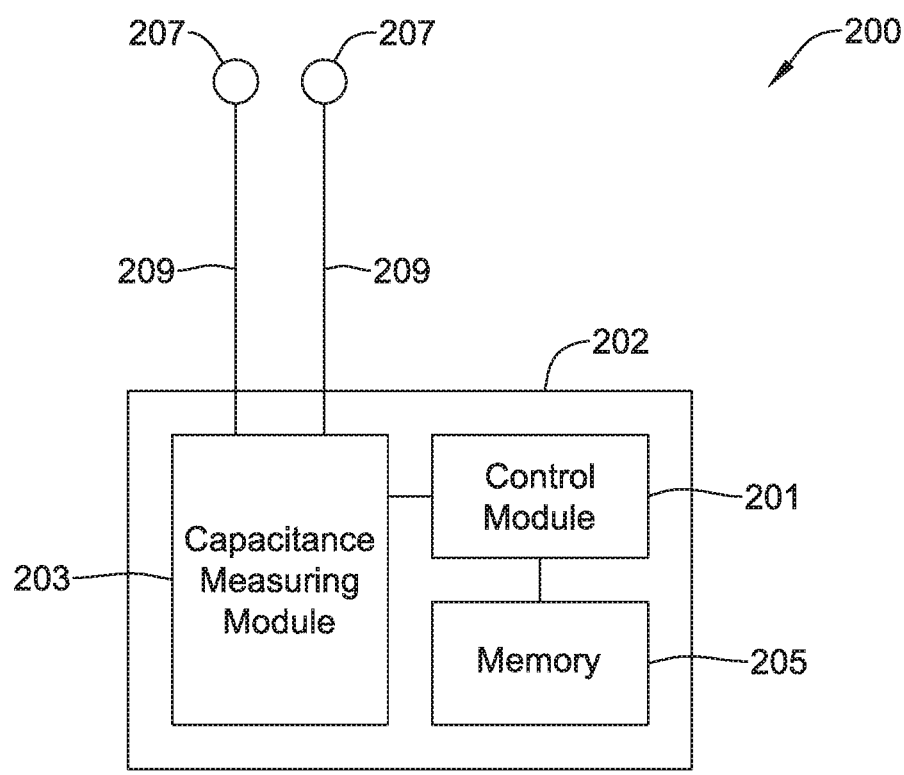
FIG. 4 is a schematic view of an exemplary control device of a fluid management system.

FIG. 4 depicts the control device 200 including a control module 201, a capacitance-measuring module 203, a memory 205, and a housing 202. The control device 200 may additionally include electrodes 207 connected to the capacitance-measuring module 203. In some embodiments, the control device 200 may additionally be connected to the pump 130 and/or the negative pressure source 125 of the fluid management system 126 in order to control fluid inflow and outflow from the fluid container 128, as will be described in more detail below.

In general, the control module 201 may include a preprogrammed chip, such as a very-large-scale integration (VLSI) chip or an application specific integrated circuit (ASIC). In such embodiments, the chip may be pre-programmed with control logic in order to control the operation of the control device 200 and any components connected to the control device 200. In other instances, the control module 201 may include a programmable microprocessor or the like.

The memory 205 be connected to the control module 201 and may store information. The control module 201 may be able to both write information to and read information from the memory 205. The memory 205 may be volatile memory, non-volatile memory, or a combination of volatile memory and non-volatile memory.

The electrodes 207 may be connected to the control device 200 via the capacitance-measuring module 203. The electrodes 207 may be attached to wires or leads 209 which extend from the housing 202. Together, the electrodes 207 and the wires 209 may generally conduct electrical signals to and from the capacitance-measuring module 203.

The capacitance-measuring module 203 may be configured to sense a capacitance through the electrodes 207. For example, capacitance-measuring module 203 may represent dedicated circuitry capable of sensing electrical signals when the electrodes 207 are connected to an object and to determine a capacitance from the sensed electrical signals. At particular time intervals, or when requested, the capacitance-measuring module 203 may communicate a measured capacitance to the control module 201.

Although depicted as separate modules or components, in some embodiments, the control module 201, the capacitance-measuring module 203, and the memory 205 may all be combined into fewer than three separate modules or even into a single module. For instance, a microcontroller or microprocessor may have dedicated memory circuitry disposed within the controller or processor and may further have the capability to sense electrical signals and determine a capacitance from the sensed electrical signals.

In some embodiments, the control module 201 may be configured to set a fluid deficit alarm threshold based on a determined capacitance. In these embodiments, the electrodes 207 may be attached to the fluid container or reservoir 128, and the capacitance-measuring module 203 may determine a capacitance of the based on sensed electrical signals from the electrodes attached to fluid container or reservoir 128. Although in such situations the electrodes 207 are not in direct contact with the fluid in fluid reservoir 128, the type of fluid, ionic or non-ionic, will have a measurable effect on the capacitance measured by the capacitance-measuring module 203. After determining a capacitance, the capacitance-measuring module 203 may communicate the capacitance to the control module 201. The control module 201 may then compare the determined capacitance to a capacitance threshold. If the control module 201 determines that the capacitance is below the threshold, then the control module 201 may determine that the fluid is an ionic fluid. If the control module 201 determines that the capacitance is equal to or greater than the capacitance threshold, then the control module 201 may determine that the fluid is a non-ionic fluid.

In response to making a determination of whether the fluid is an ionic or a non-ionic fluid, the control module 201 may set a fluid deficit alarm threshold. For example, the control module 201 may set the fluid deficit alarm threshold to be equal to between about 1.5 L and about 2.5 L after determining that the fluid is an ionic fluid. In more specific embodiments, the control module 201 may set the fluid deficit alarm threshold to be equal to 1.5 L, 2.0 L, or 2.5 L, or any other suitable value. Alternatively, the control module may set the fluid deficit alarm threshold to between about 0.5 L and about 1.0 L after determining that the fluid is a non-ionic fluid. In more specific embodiments, the control module 201 may set the fluid deficit alarm threshold to be equal to 0.5 L, 0.75 L, or 1.0 L, or any other suitable value. As will be described in more detail below, the control module 201 may further monitor a fluid deficit parameter and take action after determining that the fluid deficit parameter has crossed the fluid deficit alarm threshold.

Figure 5:
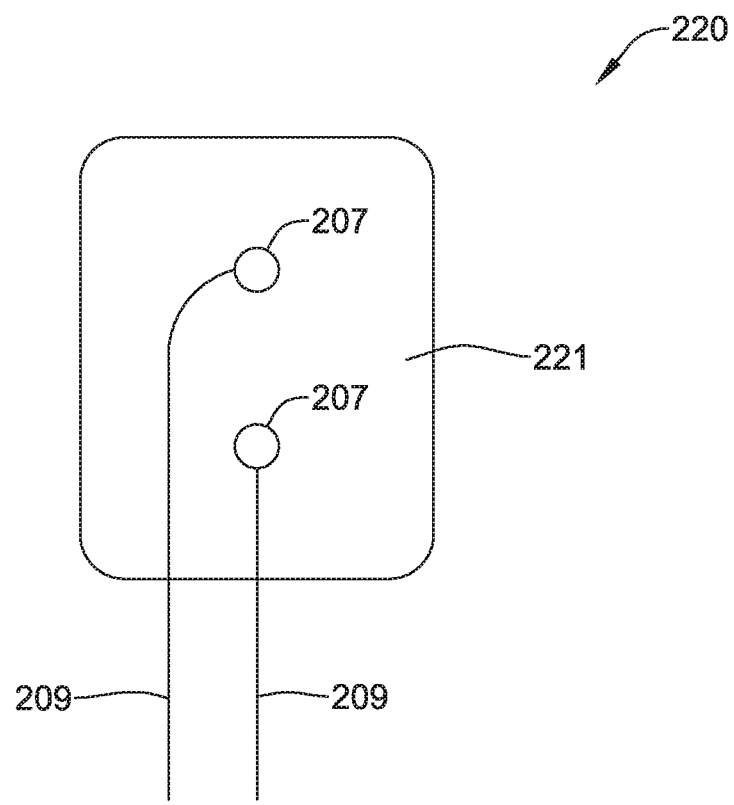
FIG. 5 is a plan view of an exemplary patch that may be used with the exemplary control device of FIG. 4.

In some further embodiments, the electrodes 207 may be incorporated into a patch or label, as shown in FIG. 5. FIG. 5 depicts the patch 220 with the electrodes 207 embedded on the side 221 of the patch 220. Generally, the patch 220 may be made from a soft, relatively flexible material. In at least some embodiments, the side 221 of the patch 220 may contain an adhesive material. The adhesive material may allow the patch 220 to be connected to a fluid reservoir of a fluid management system, such as the fluid reservoir 128, by simple application of pressure of the patch 220 against the fluid reservoir. In some alternative embodiments, instead of the capacitance-measuring module 203 being located within housing 202 of the control device 200, the capacitance-measuring module 203 may incorporated into the patch 220. In such embodiments, one or more wires or leads 209 may extend from the patch 220 to connect the capacitance-measuring module 203 to the housing 202 and/or the control module 201.

Figure 6:
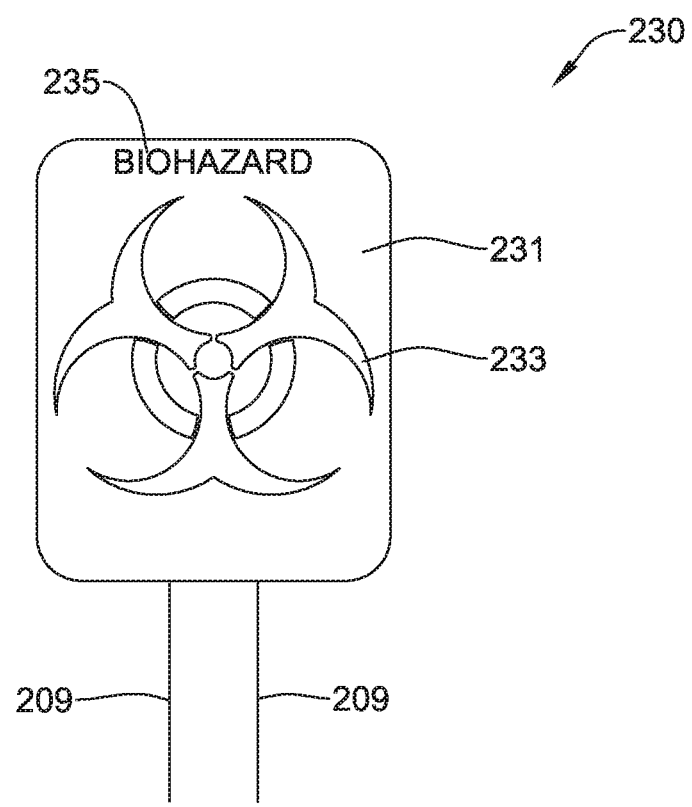
FIG. 6 is a plan view of another exemplary patch that may be used with the exemplary control device of FIG. 4.

FIG. 6 depicts another exemplary patch 230, illustrating a side 231. In general, the side 231 may be an opposing side to the side on which the electrodes 207 are disposed. In the embodiment of FIG. 6, the side 231 includes a biohazard symbol 233 along with the words "BIOHAZARD" 235. In these embodiments, when the patch 230 is connected to a fluid reservoir, the electrodes 207 may be pressed against the fluid reservoir to enable the capacitance-measuring module 203 to determine a capacitance of the fluid reservoir and the fluid and the biohazard symbol and words 233, 235 may be displayed for easy viewing.

Figure 7:
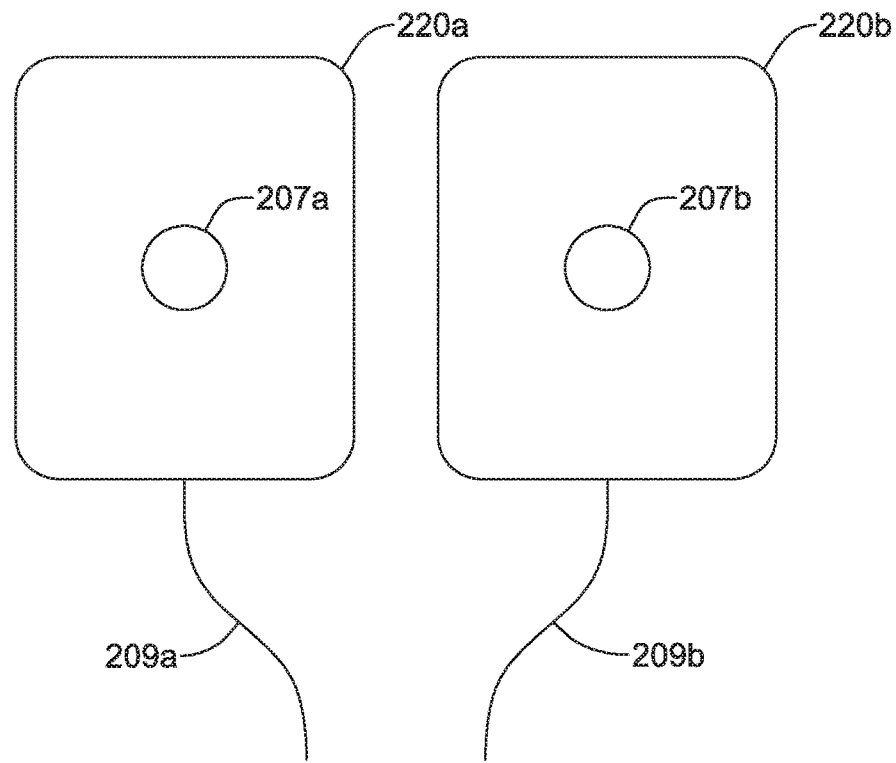
FIG. 7 is a plan view of exemplary patches that may be used with the exemplary control device of FIG. 4.

FIG. 7 depicts another exemplary embodiment where, instead of a single patch 220, control device 200 may be connected through wires 209a and 209b to two separate patches 220a and 220b. In general, patches 220a and 220b may be similar to patch 220 described with respect to FIG. 5. For instance, each of patches 220a and 220b may include at least one electrode on a first face of each patch, such as electrodes 207a and 207b depicted in FIG. 7. Accordingly, when patches 220a and 220b are placed on a fluid reservoir, control device 200 may monitor signals receives from electrodes 220a, 20b via wires 209a, 209b and determine a capacitance of the reservoir. The face of patches 220a and 220b may include an adhesive material for affixing patches 220a and 220b to the fluid reservoir. Additionally, in some embodiments, a face of patches 220a, 220b including electrodes 207a, 207b may include a biohazard symbol and/or words, as described in FIG. 6. In some of these embodiments, each of patches 220a and 220b may have a biohazard symbol on a second face opposite the first face including electrodes 207*a*, 207*b*, for instance in a manner similar to that described in FIG. 6.

Figure 8:
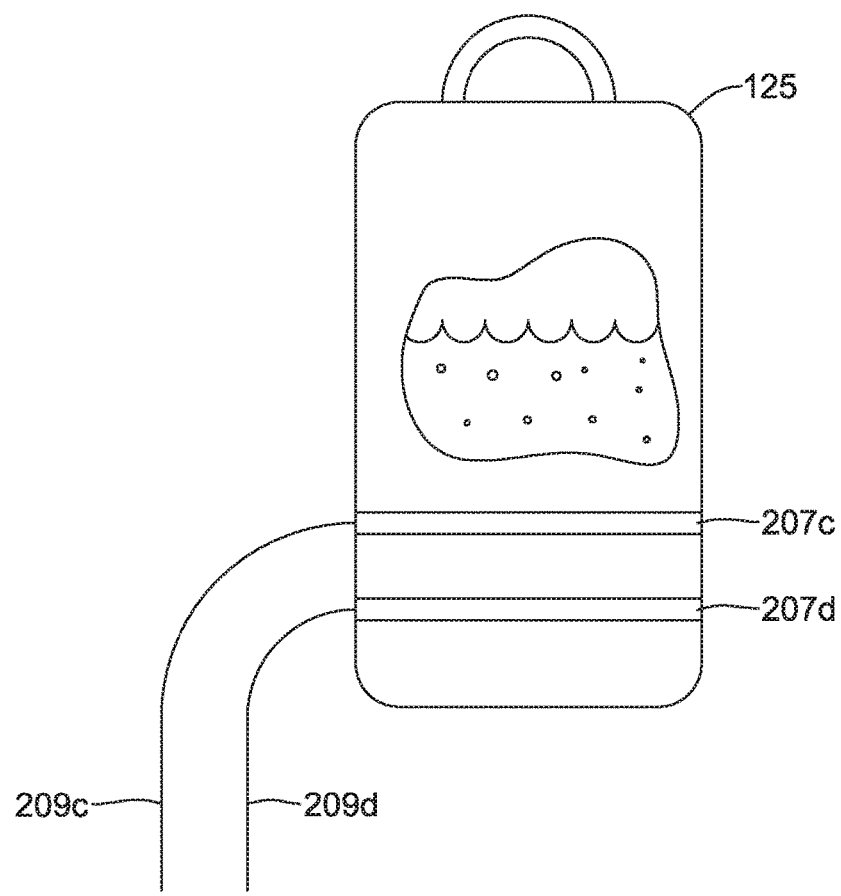
FIG. 8 is a schematic view of an exemplary fluid reservoir with embedded electrodes for connection to a control device, such as the exemplary control device of FIG. 4.

FIG. 8 is still another embodiment of electrodes 207. In the embodiment of FIG. 8, electrodes 207*c* and 207*d* may be embedded directly into fluid reservoir 128. In these embodiments, control device 200 may only include wires 209*c* and 209*d*, and not include any electrodes. Rather, a user may connect wires 209*c* and 209*d* to electrodes 207*c* and 207*d* embedded directly into reservoir 128. Once connected, control device 200 may measure the capacitance of fluid reservoir 128 by sensing signals via wires 209*c*, 209*d* and electrodes 207*c*, 207*d*.

Figure 9:
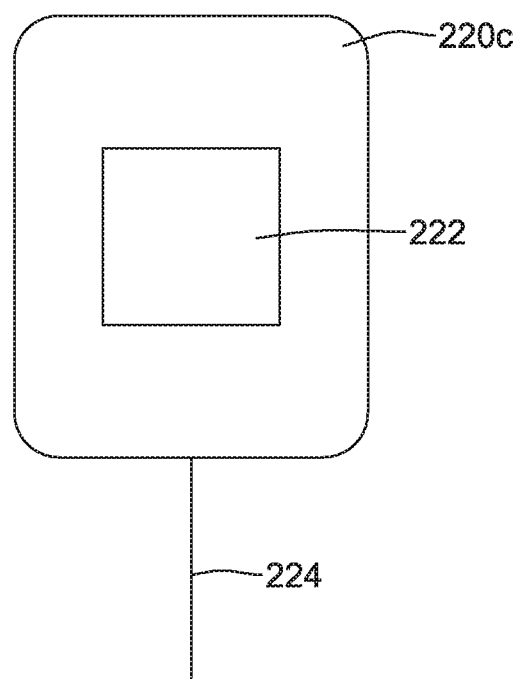
FIG. 9 is a plan view of another exemplary patch that may be used with the exemplary control device of FIG. 4.

FIG. 9 is another exemplary embodiment of a patch of control device 200. FIG. 9 depicts patch 220*c*. Patch 22*c* may be similar to patch 220 described with respect to FIG. 5, except patch 220*c* may include capacitance sensing module 222 embedded on a first surface of patch 220*c*. Instead of control device 200 sensing signals via electrodes and wires and determining a capacitance from those signals, capacitance sensing module 222 may directly determine a capacitance and communicate the determined capacitance to control device 200 via wire 224. As can be seen, in the embodiment of FIG. 9, only a single wire, wire 224, is needed to run from patch 220*c* to control device 200.

Figure 10:
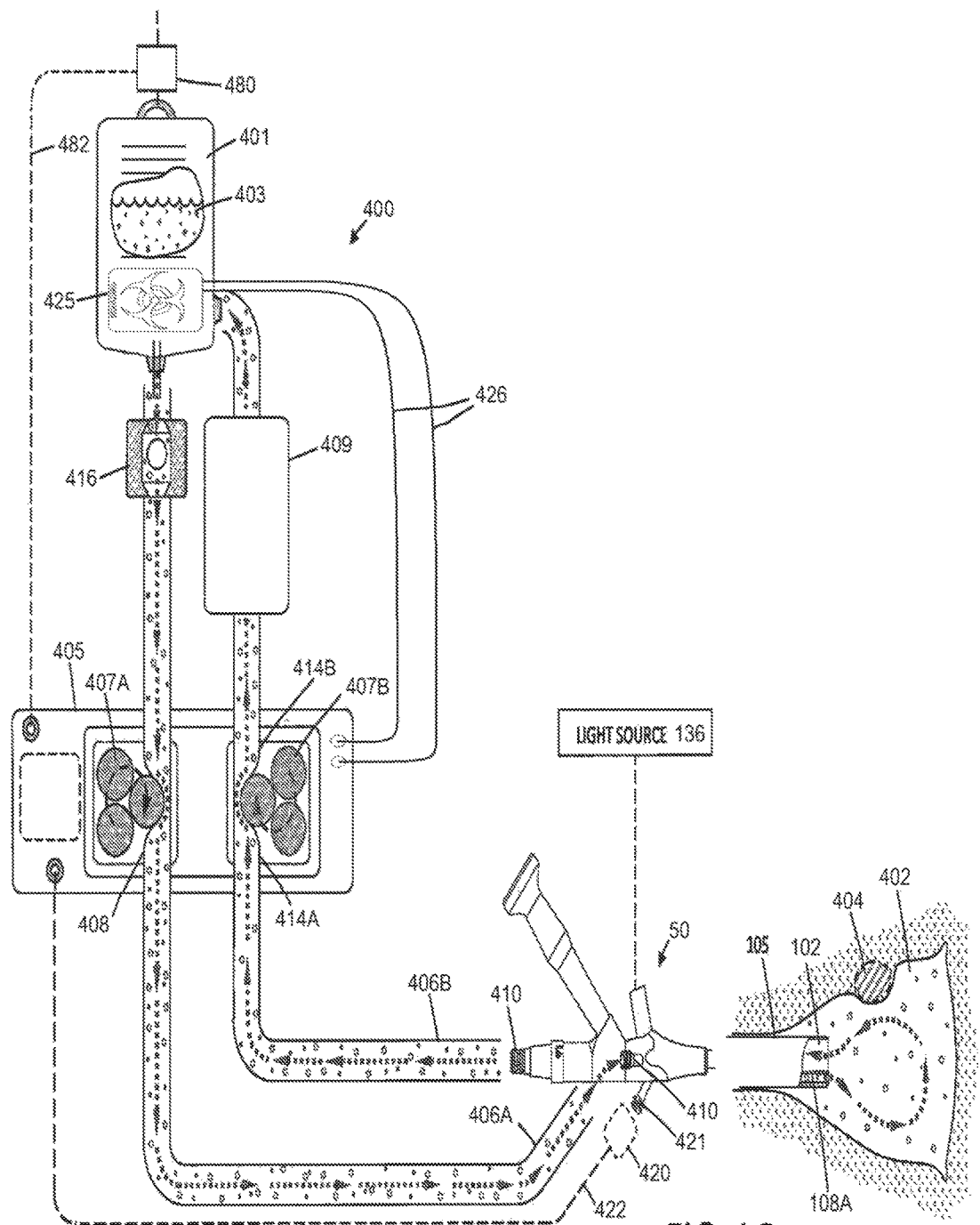
FIG. 10 is a schematic view of an exemplary fluid management system illustrated in conjunction with an endoscope.

FIG. 10 depicts another exemplary fluid management system 400 schematically in use in a medical procedure. For instance, FIG. 10 depicts fluid management system 400 in use with hysteroscope 50, which may be used to view and assess the uterine cavity 402 including fibroid 404, and with fluid source or reservoir 401 including distension fluid 403. In general, the fluid management system 400 includes lengths of tubing, such as flow lines 406A, 406B and a control device, such as control device 405. Fluid management system 400 may be connected to the fluid source or reservoir 401 containing the distension fluid 403 to control the flow of the distension fluid 403 into and out of uterine cavity 402.

In some embodiments, the fluid management system 400 may include a one-way float valve 416 in the inflow line 406A proximate distension fluid source or reservoir 401. The float valve 416 closes the inflow line when the distension fluid reservoir 401 is empty to prevent air from entering the inflow line 406A. Additional embodiments may include a similar float valve (not shown) in outflow line 406B between the second pump 407B and the filter system 409.

The control device 405 may be similar to control device 200 in some respects. For instance, control device 405 may include a control module similar to control module 201, a capacitance-measuring module similar to 203, and a patch 425 including electrodes (not shown) connected to the control device 405 via wires or leads 426. In the example of FIG. 10, control device 405 may additionally include two positive displacement (peristaltic) pumps (first infusion pump 407A, second outflow pump 407B) that are controlled by the control module of control device 405 which is configured to operate pumps 407A and 407B to provide fluid inflows and outflows adapted to maintain distension of the uterine cavity 402.

In some embodiments, fluid management system 400 may additionally include a filter system 409 for filtering distention fluid 403 that is removed from the uterine cavity 402 and thereafter returned to the fluid reservoir 401.

Accordingly, control device 405 may be configured to control peristaltic pump 407A to provide positive pressure at the outflow side 408 of the pump to provide inflows of distention fluid 403 through first flow line or inflow line 406A which is in communication with luer fitting 410 and fluid flow channel 108*a* in hysteroscope 50. The control device 405 may further control the second peristaltic pump 407B to provide negative pressure at the inflow side 414A of the pump to the second flow line or outflow line 406B to assist in providing outflows of distention fluid 403 from the uterine cavity 402. In operation, the second peristaltic pump 407B also operates to provide positive pressure on the outflow side 414B of pump 407B in the second flow line 406B to pump outflows of the distension fluid 403 through the filter system 409 and back to the fluid source 401.

In one embodiment, the control device 405 may have control algorithms that operate to control pressure in the uterine cavity 402 by pressure signals from a pressure sensor 420 that is coupled to a fitting 421 in hysteroscope 50 which communicates with another channel, such as channel 106 or flow channel 108*b* depicted in FIG. 2, that extends through the endoscope shaft 105 to the uterine cavity 402. The pressure sensor 420 is operatively coupled to control device 405 by cable 422 which sends pressure signals to the control device 405. In one embodiment, the channel 106 has a diameter large enough to allow highly accurate sensing of actual intra-cavity pressure. In other embodiments, control device 405 may estimate the intra-cavity pressure through various calculations using known flow rates through pumps 407A and/or 407B or through remote pressure sensors in the fluid inflow line and/or outflow lines.

As depicted in FIG. 3, the channel 106 in communication with the pressure sensor 420 may be independent of flow channels 108*a* and 108*b* used for inflows and outflows of distension fluid 403 into the uterine cavity 402. In the absence of fluid flows in channel 106, the fluid in the channel 106 then forms a static column of fluid (air or liquid) that transmits changes in pressure to the sensor 420 as the pressure in the uterine cavity changes. In one variation, the channel 106 has a cross-section of at least 1 mm, and fluid pressure within the pressure channel column is equivalent to the pressure in the uterine cavity. Thus, the pressure sensor 420 is capable of a direct measurement of pressure within the uterine cavity or other body cavity. In one method, the channel 106 can be purged of air by opening a valve (not shown) to release air from the channel 106 and the sensor 420.

In general, the sensor 420 may include any pressure sensor mechanism known in the art. As one example, the sensor 420 can be a biocompatible, piezoresistive silicon sensor of the type used in invasive blood pressure monitoring, such as piezoresistive silicon pressure sensor, Model No. 1620, available from Measurement Specialties. Ltd., 45738 Northport Loop West, Fremont, Calif. 94538. The sensor is designed with a pressure sensing element mounted on a ceramic substrate. A dielectric gel can be placed over the sensor element to provide electrical and fluid isolation.

In some embodiments, sensor 420 may include multiple pressure sensor mechanisms for redundancy purposes. For instance, if one pressure sensor reads a relatively significantly different value from another pressure sensor, which may be an indication that something is wrong with one of the pressure sensor mechanisms.

Additionally, sensor 420 may have a body that includes a luer fitting for connecting to hysteroscope 50 in a fluid-tight manner. In some additional embodiments, the sensor 420 may further include an air purging channel having a very small dimension that extends from inside the sensor body to outside of the sensor body. The air purging channel may have a cross-section of between about 0.0001 inches (0.00254 mm) and about 0.001 inches (0.0254 mm) for releasing air. When opened, the air purging channel will quickly release air from the system to purge the sensor 420 and channel 108b of air, but the small dimension of the channel may prevent any appreciable amount of distention fluid from leaking through the channel.

In the embodiment of FIG. 10, a selected pressure can be set at the control device 405, for example via a user interface 430 by a user, which may include a touch screen. In some embodiments, the selected pressure can be any pressure between 0 and 150 mm Hg. In one variation, the first peristaltic pump 407A is operated by the control device 405 to operate as a variable speed positive displacement pump that is actuated on demand to provide a flow rate from zero up to 1000 ml/min through inflow line 406A. In one variation, the second peristaltic pump 407B operates at a fixed speed to move the distention fluid 403 from the uterine cavity 402 through the outflow line 406B. In use, the control device 405 can operate the pumps 407A and 407B at selected matching or non-matching speeds to increase, decrease or maintain the volume of distention fluid 403 in the uterine cavity 402. Thus, by independent control of the pumping rates of the first and second positive displacement pumps 407A and 407B, a selected set pressure in the body cavity can be achieved and maintained in response to signals of actual intra-cavity pressure provided by pressure sensor 420.

User interface 430, in addition or alternatively to including a touch screen, may further include one or more foot-pedal switches which may be places apart from control device 405 but connected to control device 405. In some of these embodiments, a first foot-pedal switch may control the actuation of a tissue resecting device inserted into hysteroscope 50, such as tissue resecting device 100 of FIG. 1, while the tissue resecting device is in a resection mode. For instance, during actuation, the first foot-pedal switch may control actuation of the working end of the tissue resecting device by driving a resecting implement, reciprocating an electro-surgical implement and/or delivering electrical energy through the working end, or otherwise controlling the working ends of the resection device to resect tissue.

A second foot-pedal switch may operate the tissue resecting device in a coagulation mode. For instance, activation of the second foot-pedal switch may deliver electrical energy to the working end of the tissue resecting device without actuating any reciprocating portion of the tissue resecting device.

In some embodiments, when in the resection mode and/or the coagulation mode, activation of the first and/or section foot-pedal switches may additionally result in the inflow pump 407A and the outflow pump 407B being actuated to pump fluid into the body cavity and circulate the distention fluid 403 out of the uterine cavity. During activation of the working end of the tissue resection device 100, it may be important to maintain intra-uterine pressure sufficient enough to inflate the operating area and to circulate the distention fluid 403 into and out-of the uterine cavity 402.

User interface 430 may further include third and fourth foot-pedal switches in some embodiments. In these embodiments, the third foot-pedal switch may separately control fluid inflow into uterine cavity 402. For instance, the third foot-pedal switch may control operation of pump 407A. In some cases, the third foot-pedal switch may be a simple on/off switch which, when switched on, causes pump 407A to operate at a static flow rate. In other cases, the third foot-pedal switch may be a variable switch by which a user may be able to not only switch pump 407A on, but may also control the flow rate based on a position of the switch. The fourth foot-pedal switch may operate in a similar manner to the third foot-pedal switch, but may control the outflow pump 407B.

As mentioned, in some embodiments the control device 405 of the fluid management system 400 includes a user interface 430 that is configured to display information to a user. Some additional example information may include the intra-uterine pressure, infusion pump status, and/or a fluid deficit parameter. The fluid deficit parameter may represent an amount of fluid lost from the fluid management system 400, for instance through intravasation or other fluid loss mechanisms.

In at least some embodiments where the control device 405 is configured to display a fluid deficit parameter, the fluid management system 400 may be further configured to determine a fluid deficit parameter. In order to determine the fluid deficit parameter, the fluid management system 400 may additionally include a weight-measuring device connected to the fluid reservoir 401, for instance the weight-measuring device 480.

In some embodiments, the weight-measuring device 480 may comprise a load cell or other device configured to translate weight into an electrical signal. In other embodiments, instead of including weight-measuring device 480, the fluid management system 400 may include a sensor adapted for sensing the volume of the distention fluid 403 in the fluid reservoir 401, such as a float or level sensor in the distention fluid 403. In still other embodiments, the fluid management system 400 may include an impedance or capacitance sensor coupled to the fluid source or an optical sensor operatively coupled to the fluid reservoir 401 or any other suitable type of weight or volume sensing mechanism.

In embodiments where the fluid management system 400 includes the weight-measuring device 480, the fluid reservoir 401 may generally be hung from the weight-measuring device 480 of the fluid management system 400. The weight-measuring device 480 may be connected to the control device 405 through cable 482 and may communicate electrical signals corresponding to the weight of the fluid reservoir 401 via the cable 482 throughout a medical procedure. In some embodiments, the weight-measuring device 480 may communicate a signal representing the weight of the fluid reservoir 401, while in other embodiments the weight-measuring device 480 may communicate an electrical signal related to the weight of the fluid reservoir 401, but the control device 405 may ultimately determine the weight of the fluid reservoir 401.

Upon connection of the fluid reservoir 401 to the fluid management system 400, the fluid management system 400 may be purged of air. As one example purging method, a purge adapter may be connected between the free ends of the inflow line 108a and outflow line 108b. Thereafter, the control device 405 may implement a control algorithm to actuate the pumps 407A and 407B to pump the distention fluid 403 contained in the fluid reservoir 401 through lines 108a and 108b and filter system 409 and back to the fluid reservoir 401, which purges air from the system. In some cases, the control algorithm can operate the pumps and monitor flow volume via pump speed to determine the correct amount of flow required to fill the system with saline, which can be approximately 500 ml in some embodiments. However, it should be understood that other purging methods may be used and should be considered within the scope of this disclosure.

After purging air from the fluid management system 400, the control device 405 may make an initial measurement of the weight of the fluid reservoir 401 and may store this measurement in a memory of the control device 405. Throughout a medical procedure, the control device 405 may periodically or continuously monitor the signals communicated from the weight-measuring device 480 in order to determine a current weight of the fluid reservoir 401. The control device 405 may then compare a difference between the initial weight and the current weight to determine a weight difference. The control device 405 may then translate this weight difference into a fluid deficit parameter, representing a volume of fluid that has been lost from the fluid management system. In other embodiments, the control device 405 may determine an initial volume parameter from the initial weight and a current volume parameter from the current weight parameter, and take the difference between these volume parameters to determine the fluid deficit parameter.

In a similar manner to that described with respect to the control device 200, the control device 405 may automatically determine and set a fluid deficit alarm threshold. For instance, the control device 405 may receive electrical signals from the patch 425 either representing a determined capacitance or signals indicative of a capacitance from which the control device 405 determines a capacitance. The control device 405 may then compare the determined capacitance to a capacitance threshold to determine if distension fluid 403 is an ionic fluid or a non-ionic fluid. Based on this determination, the control device 405 may set the fluid deficit alarm threshold at an appropriate value, for instance as described with respect to control device 200.

The control device 405 may further continuously compare the fluid deficit parameter to the fluid deficit alarm threshold. As long as the fluid deficit parameter is less than the fluid deficit alarm threshold, the control device 405 may not take any action related to this measurement. However, once the control device has determine that the fluid deficit parameter has equaled or exceeded the fluid deficit alarm threshold, the control device 405 may output an alarm signal.

In some embodiments, the alarm signal may cause the user interface 430 to display one or more warning symbols or messages indicating that the fluid deficit parameter has equaled or exceeded the fluid deficit alarm threshold. In some embodiments, the user interface 430 may include a speaker. In at least some of these embodiments, the alarm signal may cause the speaker to emit an audible alarm indicating that the fluid deficit parameter has equaled or exceeded the fluid deficit alarm threshold. In still additional, or alternative embodiments, the alarm signal may cause the control device 405 to cease pumping the distension fluid 403 into uterine cavity 402, for example by disabling pump 407A. In different embodiments, the alarm signal may cause any combination of these functions. In still some additional, or alternative, embodiments, the control device 405 may additionally allow reception of input into user interface 430 to override the alarm signal. In some alternative embodiments, the control device 405 may simply disallow operation of the fluid management system 400 if the control device 405 determines that the fluid is a non-ionic fluid. For instance, the control device 405 may prevent pumps 407A, 407B from operating.

As mentioned, aside from using user interface 430 to display warnings or audible alarms, the control device 405 may display the fluid deficit parameter at user interface device 430 so the user has an up-to-date knowledge of the fluid deficit parameter. In some additional embodiments, the control device 405 may be configured to output fluid deficit notification signals periodically to the user interface 430. For instance, the control device 405 may be configured to compare the current fluid deficit parameter to one or more fluid deficit notification thresholds. In some embodiments, these fluid deficit notification thresholds may be set at increments of 50 mL, for instance at 50 mL, 100 mL, 150 mL, and so on. In other embodiments, the fluid deficit notification thresholds may be set at increments of 100 mL, 150 mL, 200 mL, 250 mL, 500 mL, or any other suitable increment. Once the fluid deficit parameter has crossed one of these fluid deficit notification thresholds, the control device 405 may output a fluid deficit notification signal. In some embodiments, the fluid deficit notification signal may cause user interface 430 to display a notification, for instance a message or provide a flashing indication. In other embodiments, the fluid deficit notification signal may cause user interface 430 to emit an audible notification, such as a beep or other notification sound. In still other embodiments, the fluid deficit notification signal may cause the control device 405 to cease pumping distension fluid 403 into the uterine cavity 402 and to display a notification on the user interface 430. In these embodiments, the control device 405 may additionally accept input at the user interface device 430 from a user overriding the fluid deficit notification signal causing the control device 405 to resume normal operation. Of course, in additional, or alternative, embodiments, the fluid deficit notification signal may cause any combination of these actions.

Additionally, although the control device 405 is depicted in use with a closed-loop fluid management system, it should be understood that such a device may be useable with open-loop fluid management systems. In such embodiments, the control device 405 may similarly make an ionic or non-ionic determination of the fluid in the open-loop fluid management system reservoir. Additionally, the control device 405 may take an initial measurement, e.g. weight or volume, of the reservoir. Throughout the procedure, the control device 405 may then add a current measurement of the reservoir and a current measurement of a waste system of the open-loop fluid management system, which collects used distension fluid, and compare the added values to the initial measured value of the reservoir. The difference between these values may be the fluid deficit parameter representing the loss of fluid in the open-loop fluid management system. The control device 405 may additionally compare the fluid deficit parameter to thresholds, as described with respect to the closed loop fluid management system.

Figure 11:
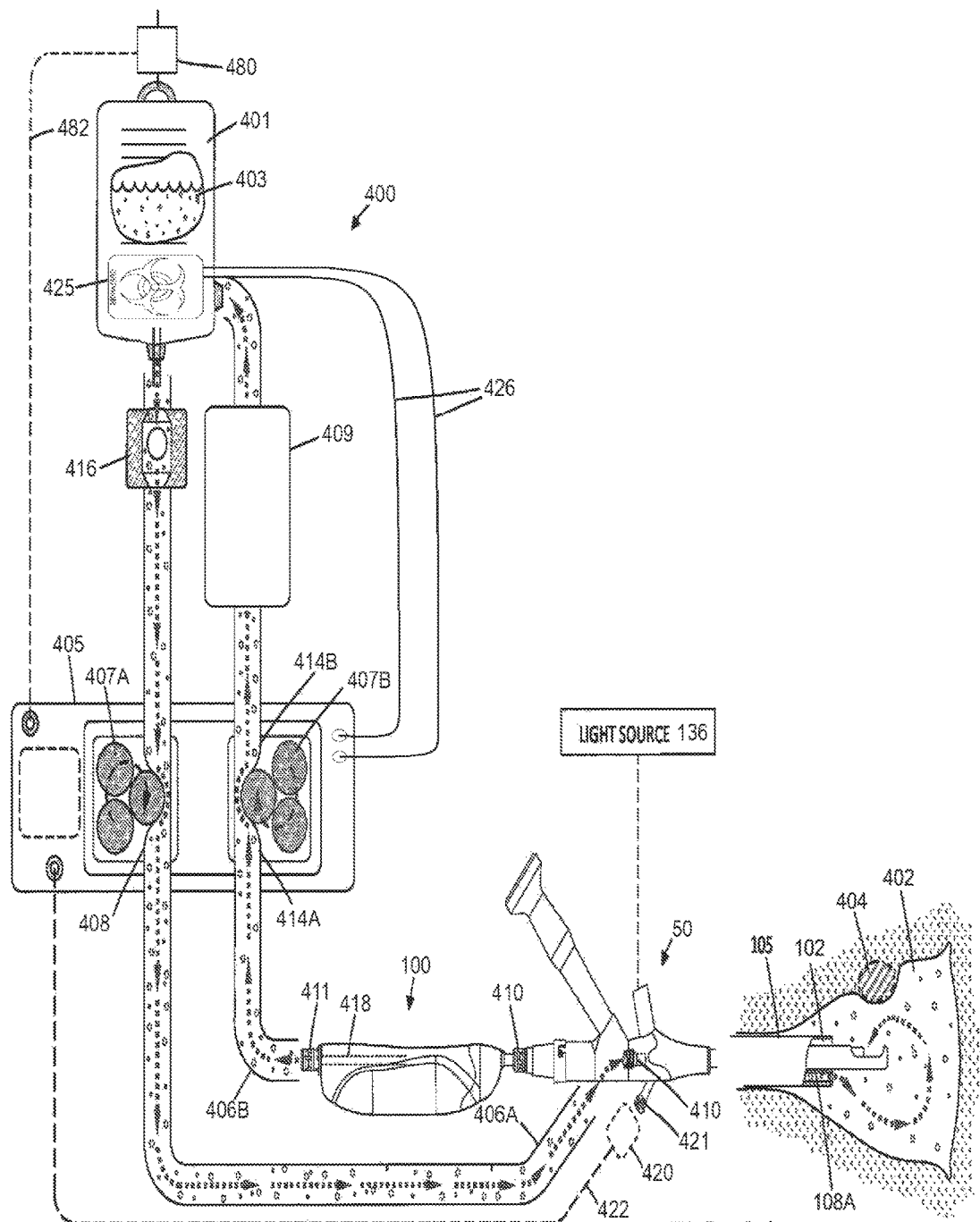
FIG. 11 is a schematic view of the fluid management system of FIG. 10 illustrated in conjunction with an endoscope and a resecting device.

FIG. 11 schematically illustrates exemplary fluid management system 400 in operation during a medical procedure similar to that shown in FIG. 9, but including a tissue-resecting device 100. As can be seen in FIG. 8, the tissue resecting device 100 of FIG. 1 has been introduced through the working channel 102 of the hysteroscope 50 into the uterine cavity 402. The outflow tubing portion 406B is coupled to the quick-connect fitting 411 of the resecting device 100 and thus the fluid pathway for outflows is through the extraction channel 418 of the resecting device 100.

Figure 12:
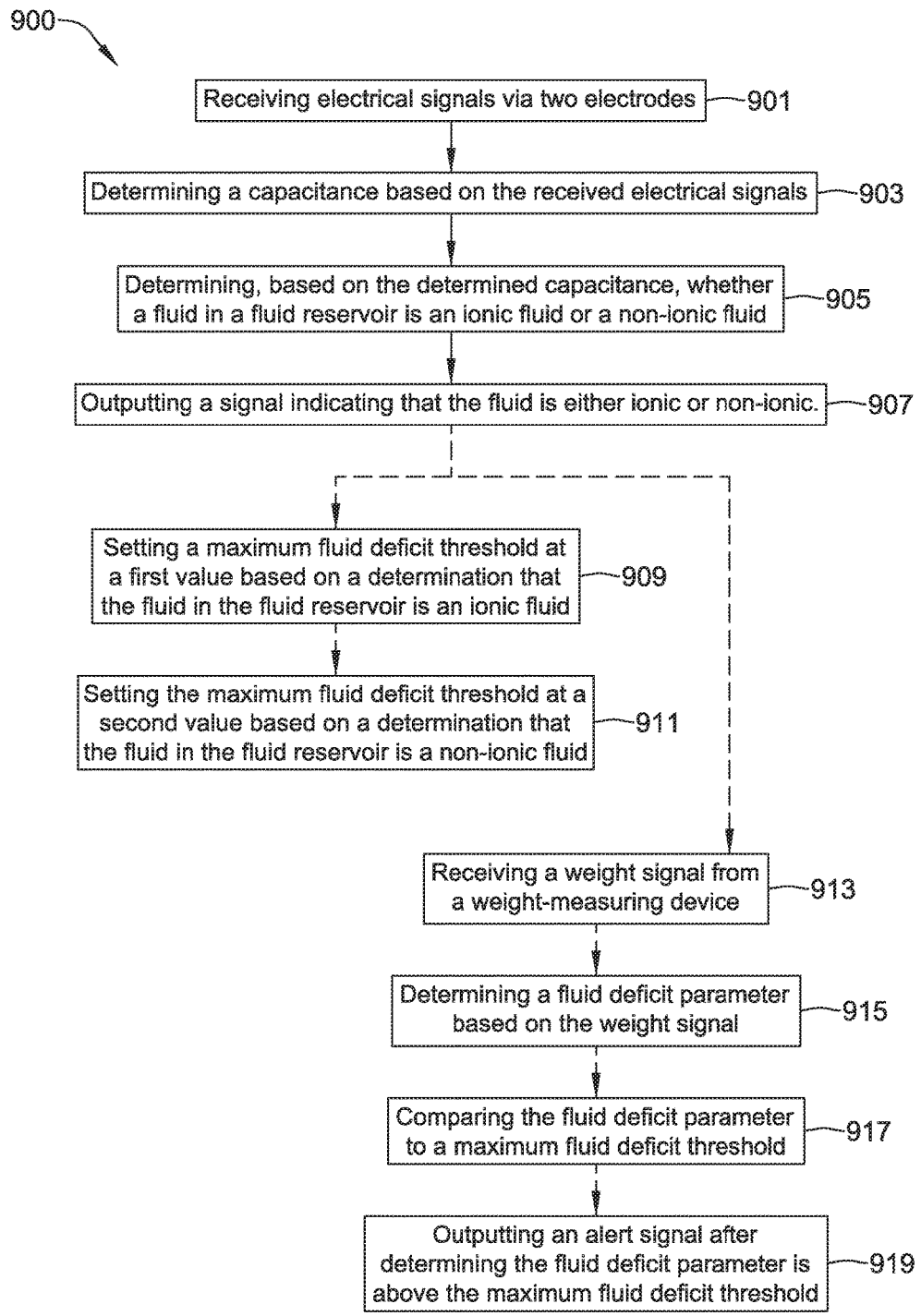
FIG. 12 is a flow diagram of an exemplary fluid management method of the present disclosure.

FIG. 12 is a flow diagram of an exemplary fluid management method 900. Although the method 900 will be described with respect to fluid management system 400 and control device 405, it should be understood that method 900 may be performed by other fluid management systems and/or control devices that have differing features than fluid management system 400 and/or control device 405.

Accordingly, the control device 405 may begin with receiving electrical signals via two electrodes, as at 901. These electrical signals may be received from, for example, one or more electrodes or from a capacitance-measuring device or module. Once the control device 405 has received the electrical signals, the control device 405 may determine a capacitance based on the received electrical signals, as at 903. As described previously, the received electrical signals may be used by the control device 405 in determining or calculating a capacitance. However, in alternative embodiments, the control device 405 may receive a determined capacitance, for instance from a capacitance-measuring device or module. In such embodiments, the control device 405 may not perform step 903. Rather, step 903 may be performed by a separate device or module.

After the capacitance has been determined, the control device 405 may determine, based on the determined capacitance, whether a fluid in a fluid reservoir is an ionic fluid or a non-ionic fluid, as at 905. For instance, the control device 405 may compare the determined capacitance to a capacitance threshold. If the control device 405 determines that the capacitance is below the threshold, then the control device 405 may determine that the fluid is an ionic fluid. If control device 405 determines that the capacitance is equal to or greater than the capacitance threshold, then the control device 405 may determine that the fluid is a non-ionic fluid.

Finally, the control device 405 may output a signal indicating that the fluid is either ionic or non-ionic, as at 907. In some embodiments, the control device 405 may output the signal for storage in a memory. In additional or alternative embodiments, the output signal may cause a user interface to display the determination that the fluid is ionic or non-ionic. In still additional or alternative embodiments, the output signal may prevent one or more pumps of the fluid management system from operating, for instance in situations where the type of fluid is incompatible with the fluid management system.

In some embodiments, the method may include one or more additional steps. For example, the method may include steps 909 and 911. In such embodiments, the control device 405 may additionally set a maximum fluid deficit threshold at a first value based on a determination that the fluid in the fluid reservoir is an ionic fluid, as at 909, and set the maximum fluid deficit threshold at a second value based on a determination that the fluid in the fluid reservoir is a non-ionic fluid, as at 911. In at least some of these embodiments, the first value and the second value are different.

In alternative embodiments, the method 900 may include steps 913, 915, 917, and 919. In these alternative embodiments, the control device 405 may additionally receive a weight signal from a weight-measuring device, as at 913. For example, the fluid management system may additionally include a weight-measuring device or module, such as any of those described with respect to fluid management system 400. In these embodiments, the weight-measuring device or module may communicate a determined weight or electrical signals indicative of a weight to control device 405. The control device 405 may then determine a fluid deficit parameter based on the weight signal, as at 915. The fluid deficit parameter may, for example, represent a volume of fluid that has been lost from the fluid management system. The control device 405 may further compare the fluid deficit parameter to a maximum fluid deficit threshold, as at 917. For instance, the maximum fluid deficit threshold may represent a maximum safe amount of fluid that may be lost from the fluid management system if all of the fluid loss is due to fluid intravasation.

Finally, the control device 405 may output an alert signal after determining the fluid deficit parameter is above the maximum fluid deficit threshold, as at 919. For example, the control device 405 may periodically or continuously compare a fluid deficit parameter to the maximum fluid deficit threshold. In some embodiments, the alarm signal may cause a user interface, such as user interface 430 of fluid management system 400, to display one or more warning symbols or messages indicating that the fluid deficit parameter has equaled or exceeded the fluid deficit alarm threshold. In embodiments where the user interface 430 includes a speaker, the alarm signal may cause the speaker to emit an audible alarm indicating that the fluid deficit parameter has equaled or exceeded the fluid deficit alarm threshold. In still additional, or alternative embodiments, the alarm signal may cause the control device 405 to cease pumping the distension fluid 403 into uterine cavity 402, for example by disabling pump 407A. In different embodiments, the alarm signal may cause any combination of these functions. In still some additional, or alternative, embodiments, the control device 405 may additionally allow reception of input into user interface 430 to override the alarm signal. In some alternative embodiments, the control device 405 may simply disallow operation of the fluid management system 400 if the control device 405 determines that the fluid is a non-ionic fluid. For instance, the control device 405 may prevent pumps 407A, 407B from operating.

Although steps 907, 909, and 911, and steps 913, 915, 917, and 919 have been presented as alternative options for method 900, it should also be understood that in still additional embodiments, all steps 901-919 may be combined into a single method. For instance, in some embodiments of method 900, the control device 405 may perform all of the steps of FIG. 9, but this is not required in all embodiments of method 900.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. A fluid management device comprising:
 a capacitance sensor; and
 a controller connected to the capacitance sensor, the controller configured to:
  receive signals from the capacitance sensor;
  determine whether a fluid in a fluid reservoir is an ionic fluid or a non-ionic fluid based on capacitance signals received from the capacitance sensor;
  wherein the controller determines that the fluid in the fluid reservoir is an ionic fluid if the capacitance is lower than a threshold, and
  wherein the controller determines that the fluid in the fluid reservoir is a non-ionic fluid if the capacitance is greater than or equal to the threshold; and
  automatically set a fluid deficit alarm threshold based on a determination of whether the fluid in the fluid reservoir is an ionic fluid or a non-ionic fluid.

2. The fluid management device of claim 1, wherein the fluid deficit alarm threshold has a first value if the controller determined the that the fluid in the fluid reservoir is an ionic fluid and the fluid deficit alarm threshold has a second value if the controller determined that the fluid in the fluid reservoir is a non-ionic fluid, wherein the first value and the second value are different.

3. The fluid management device of claim 2, wherein the first value is between about 2 liters and about 3 liters, and wherein the second value is between about 0.5 L and 1.5 liters.

4. The fluid management device of claim 1, wherein the capacitance sensor includes a patch.

5. The fluid management device of claim 4, wherein a surface of the patch comprises a biohazard symbol.

6. The fluid management device of claim 4, wherein the patch is an adhesive patch.

7. The fluid management device of claim 1, wherein the capacitance sensor directly determines a capacitance value which is then transmitted to the controller.

8. The fluid management device of claim 1, wherein the capacitance sensor includes two spaced-apart electrodes, the controller receives signals from the two spaced-apart electrodes, and determines a capacitance from the signals from the two spaced-apart electrodes.

9. The fluid management device of claim 1, wherein the controller is further configured to:
determine a fluid deficit value;
compare the fluid deficit value to the fluid deficit alarm threshold; and
output an alarm signal after determining that the fluid deficit value is greater than the fluid deficit alarm threshold.

10. The fluid management device of claim 9, wherein the alarm signal is configured to perform one or more of:
cause a user interface device to display an indication the fluid deficit value has reached or exceeded the fluid deficit alarm threshold;
cause a user interface device to generate an audible alarm;
prevent fluid from being pumped out of the fluid reservoir.

11. The fluid management device of claim 1, further comprising a weight-measuring device connected to the controller, wherein the controller is further configured to determine a fluid deficit value based on signals received from the weight-measuring device.

12. A fluid management system comprising:
a weight-measuring device;
a capacitance sensor; and
a controller connected to the capacitance sensor and to the weight-measuring device, the controller configured to:
receive signals from the capacitance sensor and from the weight-measuring device;
determine whether a fluid in a fluid reservoir is an ionic fluid or a non-ionic fluid based on signals received from the capacitance sensor indicative of a measured capacitance of the fluid,
wherein the controller determines that the fluid in the fluid reservoir is an ionic fluid if the measured capacitance is lower than a threshold and the controller determines that the fluid in the fluid reservoir is a non-ionic fluid if the measured capacitance is greater than or equal to the threshold;
automatically set a fluid loss alarm threshold based on a determination of whether the fluid in the fluid reservoir is an ionic fluid or a non-ionic fluid;
determine a fluid loss parameter based on signals received from the weight-measuring device;
compare the fluid loss parameter to the fluid loss alarm threshold; and
generate an indication the fluid loss parameter has exceeded the fluid loss alarm threshold after determining the fluid loss parameter is greater than the fluid loss alarm threshold.

13. The fluid management system of claim 12, wherein the fluid loss alarm threshold has a first value if the controller determined the that the fluid in the fluid reservoir is an ionic fluid and the fluid loss alarm threshold has a second value if the controller determined that the fluid in the fluid reservoir is a non-ionic fluid, wherein the first value and the second value are different.

14. The fluid management system of claim 12, wherein the fluid loss parameter is based on a difference in a previous weight signal received from the weight-measuring device and a current weight signal received from the weight-measuring device.

15. The fluid management system of claim 12, further comprising a pump connected to the controller, and wherein the indication comprises the controller preventing the pump from pumping.

16. The fluid management system of claim 12, further comprising a user interface device connected to the controller, and wherein the indication comprises displaying, at the user interface device, an indication that the fluid loss parameter has exceeded the fluid loss alarm threshold.

17. The fluid management system of claim 12, further comprising a patch, the patch containing the capacitance sensor separated by a distance.

18. A fluid management method comprising:
receiving a signal from a capacitance sensor in electrical communication with a fluid provided by a fluid bag;
determining a capacitance of the fluid based on the received signal;
determining, based on a determined capacitance, whether the fluid provided by the fluid bag is an ionic fluid or a non-ionic fluid,
wherein a controller determines that the fluid provided by the fluid bag is an ionic fluid if the capacitance is lower than a threshold and the controller determines that the fluid provided by the fluid bag is a non-ionic fluid if the capacitance is greater than or equal to the threshold; and
outputting a signal indicating that the fluid is either ionic or non-ionic,
further comprising setting a maximum fluid deficit threshold at a first value based on a determination that the fluid provided by the fluid bag is an ionic fluid and setting the maximum fluid deficit threshold at a second value based on a determination that the fluid provided by the fluid bag is a non-ionic fluid,
wherein the first value is greater than the second value.

19. The fluid management method of claim 18, further comprising:
receiving a weight signal from a weight-measuring device;
determining a fluid deficit parameter based on the weight signal;
comparing the fluid deficit parameter to the maximum fluid deficit threshold; and
outputting an alert signal after determining the fluid deficit parameter is above the maximum fluid deficit threshold.

20. The fluid management method of claim 18, wherein the capacitance sensor is incorporated within a patch adhered to an exterior of the fluid bag.

* * * * *